United States Patent [19]

Greco et al.

[11] Patent Number: 4,996,300

[45] Date of Patent: Feb. 26, 1991

[54] PREPARATION OF RARE EARTH ALKOXIDES USING CATALYST

[75] Inventors: Carl C. Greco, Garnerville; Johst H. Burk, Mohegan Lake, both of N.Y.

[73] Assignee: Akzo America Inc., New York, N.Y.

[21] Appl. No.: 200,471

[22] Filed: May 31, 1988

[51] Int. Cl.$^5$ .............................................. C07F 5/00
[52] U.S. Cl. .................................... 534/15; 502/226; 502/343
[58] Field of Search ........................................ 534/15

[56] References Cited

U.S. PATENT DOCUMENTS

| | | | |
|---|---|---|---|
| 3,278,571 | 10/1966 | Mazdiyasni et al. | 534/15 |
| 3,356,703 | 12/1967 | Mazdiyasni et al. | 534/15 |
| 3,757,412 | 9/1973 | Mazdiyasni et al. | 534/15 |

OTHER PUBLICATIONS

Pauling, *College Chemistry*, Pub. by W. H. Freeman & Co., San Francisco, Calif., (1951), p. 90.
Inorganic Chemistry, vol. 5 (1965), pp. 342–346.
Inorganic Chemistry, vol. 9 (1970), pp. 2783–2787.

*Primary Examiner*—Patrick P. Garvin
*Attorney, Agent, or Firm*—Richard P. Fennelly; Louis A. Morris

[57] ABSTRACT

The reaction of rare earth metals and alcohols, to form rare earth alkoxides, is catalyzed by the use of a zinc-containing catalyst, e.g., zinc and/or zinc chloride.

10 Claims, No Drawings

PREPARATION OF RARE EARTH ALKOXIDES USING CATALYST

BACKGROUND OF THE INVENTION

1. Field of the invention

The present invention relates to a catalytic process for the manufacture of rare earth alkoxides.

2. Description of the Prior Art

A number of prior art references speak of the preparation of rare earth alkoxides using mercury compounds as catalysts. For example, U.S. Pat. No. 3,278,571 mentions the use of mercuric chloride as a catalyst, and U.S. Pat. No. 3,757,412 mentions the use of mercuric iodide or a mixture of mercuric chloride and mercuric acetate. Certain literature references also mention the use of mercury compounds as catalytic agents in the formation of rare earth alkoxides by reaction of an alcohol and the rare earth metal. Inorganic Chemistry, Vol. 5 (1965) pp. 342-346 discloses mercuric chloride as a catalyst for such a reaction. Inorganic Chemistry, Vol. 9 (1970) pp. 2783-2787 also mentions the use of mercuric chloride. Use of such mercury compounds as catalysts produces mercury metal as a by-product and is of serious potential concern from an environmental viewpoint in view of the toxicity of mercury metal and the need to insure its safe recovery if used.

SUMMARY OF THE PRESENT INVENTION

The present invention relates to the preparation of rare earth alkoxides without the use of a mercury compound as a catalyst. The present process relies upon the use of a zinc-containing catalyst for the reaction of a rare earth and an alcohol to form the desired rare earth alkoxide.

DETAILED DESCRIPTION OF THE PRESENT INVENTION

The present process is directed to the preparation of rare earth alkoxides by the reaction of a rare earth metal with an appropriate alcohol. The rare earth metals include those of the lanthanum series (Atomic Nos. 57-71) as well as the element yttrium.

The type of alcohols which can be reacted with the foregoing rare earth metals are also known to persons of ordinary skill in the art and include the straight and branched chain aliphatic alcohols including isopropanol. Generally speaking, the carbon chain length of the alkyl group of such alcohols can range anywhere from about 1 to about 10 carbon atoms.

The molar ratio of rare earth metal to alcohol which can be used in accordance with the present invention can range from about 1:3 to about 1:6, in accordance with conventional practice. The reaction can be conducted at temperatures ranging from about 80° C., to about 150° C.

The present invention includes, as an essential element, the use of a zinc-containing catalyst to catalyze the reaction of the rare earth metal and the alcohol. If desired, zinc metal can be used either along or in combination with such anhydrous inorganic zinc salts, such as zinc chloride. The use of hydrated inorganic zinc salts (such as zinc nitrate and the hydrated forms of zinc sulfate) should be avoided since their water content will bring about the undesired hydrolysis of the desired alkoxide product. The zinc-containing catalysts of this invention can be milled with the metal and then reacted with the alcohol. Alternatively, the metal can be milled alone and then reacted with a mixture of the zinc-containing catalyst and alcohol. Generally speaking, the catalytic amount of the zinc compound which is utilized can range up to about 5%, e.g., from about 1% to about 5%, by weight of the reactants.

The foregoing invention is further illustrated by the following Examples.

EXAMPLE 1

To a one liter stainless steel ball mill were added 25 grams of yttrium, 0.5 grams of zinc powder and 875 grams of stainless steel balls. The components were milled for 10 hours at 25° C. The mill was opened, and the contents were sieved through a 30 mesh screen. Yield: 20.5 grams.

To a one liter, 3-neck flask was added the above-described yttrium-zinc composition. To this was added 500 cc of fresh, dry isopropanol. The resulting mixture was heated to reflux during which there was a vigorous evolution of hydrogen. The mixture was heated at reflux for 8 hours and then allowed to cool to room temperature. The reaction mixture was filtered through diatomaceous earth (CELITE brand) using an airless filtering flask. The filtrate was collected and distilled at reduced pressure (30-50 millimeters of Hg) to remove the solvent. A viscous semi-solid remained which solidified upon standing. Yield: 21 grams (Theory: 59.6), 35% yield.

COMPARATIVE EXAMPLE 2

The same reaction was done exactly the same way except no zinc was milled with the yttrium. The milled yttrium was reacted with isopropanol in the same way. There was very little evolution of hydrogen and work-up of the reaction solutions gave a yield of less than 10% for yttrium isopropoxide.

EXAMPLE 3

To a one liter stainless steel ball mill were added 25 grams of yttrium metal, 0.7 gram of zinc powder, 0.8 gram of $ZnCl_2$ and 875 grams of stainless steel balls. The components were milled at room temperature for 12 hours. Separation of the milled reactants from the steel balls yielded 25 grams of a solid. This 25 grams of material was placed in a one liter, 3-neck flask along with 500 cc of isopropanol. The reaction mixture was heated to reflux and maintained at reflux for 24 hours. During this time a great deal of hydrogen was given off from the reaction. The reaction mixture was distilled to dryness to remove he alcohol and then the residue was dissolved in toluene. The toluene solution was filtered through diatomaceous earth (CELITE brand) using an airless filtering flask. The filtrate was collected and distilled at reduced pressure to remove the toluene. A viscous semi-solid remained which solidified on heating at 100° C. under a vacuum of 1 milliliter. Yield: 50 grams, 68% yield.

EXAMPLE 4

The same procedure described in Example 3 was utilized except that $ZnCl_2$ was substituted for zinc metal but was not milled with the yttrium. The milled yttrium, without zinc metal or zinc chloride, was reacted with a solution of isopropanol (500 cc) and 3 grams of $ZnCl_2$ over a 24 hour period. Work-up of the reaction mixture yielded 41.6 grams (a 70% yield) of yttrium isopropoxide.

The foregoing Examples have been presented to illustrate certain preferred embodiments of the present invention and should not be construed in a limiting sense. The scope of protection that is sought is set forth in the claims which follow.

We claim:

1. A catalytic process for the manufacture of rare earth alkoxides by the reaction of a rare earth metal and an alcohol in the presence of a catalytically effective amount of a zinc-containing catalyst for the reaction.

2. A process as claimed in claim 1 wherein the catalyst is zinc metal.

3. A process as claimed in claim 1 wherein the catalyst is an anhydrous zinc salt.

4. A process as claimed in claim 3 wherein the catalyst is zinc chloride.

5. A process as claimed in claim 1 wherein the catalyst is present at from about 1% to about 5%, by weight of the reactants.

6. A process as claimed in claim 5 wherein the catalyst is selected from the group consisting of zinc metal and the anhydrous zinc salts.

7. A process as claimed in claim 6 wherein the zinc salt is zinc chloride.

8. A process as claimed in claim 1 wherein the catalyst is present at from about 1% to about 5%, by weight of the reactants, and is selected from the group consisting of zinc metal and the anhydrous zinc salts, and where the mole ratio of rare earth metal to alcohol is from about 1:3 to about 1:6.

9. A process as claimed in claim 8 wherein the catalyst is zinc chloride.

10. A process as claimed in claim 8 wherein the temperature of reaction is from about 80° C., to about 150° C.

* * * * *